United States Patent [19]

Hiyama et al.

[11] Patent Number: 4,501,909

[45] Date of Patent: Feb. 26, 1985

[54] AMINOPOLYOL DERIVATIVES

[75] Inventors: Tamejiro Hiyama; Kazuhiro Kobayashi, both of Sagamihara, Japan

[73] Assignee: Sagami Chemical Research Center, Tokyo, Japan

[21] Appl. No.: 599,440

[22] PCT Filed: Aug. 12, 1983

[86] PCT No.: PCT/JP83/00263

§ 371 Date: Apr. 4, 1984

§ 102(e) Date: Apr. 4, 1984

[87] PCT Pub. No.: WO84/00755

PCT Pub. Date: Mar. 1, 1984

[30] Foreign Application Priority Data

Aug. 12, 1982 [JP] Japan .................................. 57-139196

[51] Int. Cl.³ ........................................... C07D 317/72
[52] U.S. Cl. .................................... 549/342; 549/451; 549/452
[58] Field of Search ...................... 549/451, 452, 342

[56] References Cited

U.S. PATENT DOCUMENTS 4,424,370 1/1984 Kleeman et al. .................... 549/452

*Primary Examiner*—Ethel G. Love
*Attorney, Agent, or Firm*—Wenderoth, Lind & Ponack

[57] ABSTRACT

This invention provides novel aminopolyol derivative represented by the general formula

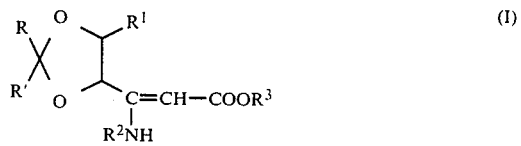

wherein each of R and R' represents a hydrogen atom, or an alkyl or aryl group or R and R', taken together, form an alkylene group, $R^1$ represents a lower alkyl group, $R^2$ represents a hydrogen atom or an acyl group, and $R^3$ represents a lower alkyl group; and a process for production thereof.

The aminopolyol derivatives of formula (I) are useful as intermediates for the synthesis of amino sugars such as 3-epi.daunosamine, acosamine, ristosamine and daunosamine which is the sugar moiety of daunomycin useful as an anti-cancer agent.

8 Claims, No Drawings

AMINOPOLYOL DERIVATIVES

FIELD OF TECHNOLOGY

This invention relates to novel aminopolyol derivatives, and more specifically to compounds represented by the following general formula

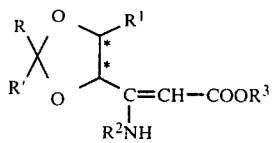

$$(I)$$

wherein each of R and R' represents a hydrogen atom or an alkyl or aryl group, or R and R', taken together, form an alkylene group, $R^1$ represents a lower alkyl group, $R^2$ represents a hydrogen atom or an acyl group, and $R^3$ represents a lower alkyl group, and a process for production thereof.

The aminopolyol derivatives of general formula (I) are useful as intermediate compounds which can be converted to aminosugars such as daunosamine (which is the sugar moiety of daunomycin useful as an anti-cancer agent), 3-epi.daunosamie, acosamine or ristosamine (see Examples A to E given hereinbelow and Topic in Antibiotic Chemistry, Ellis Horwood, Ltd., Chichester, Vol. 2, pages 99–239, PART C, "Daunomycin and Related Antibiotics" by Federico Arcamone).

BACKGROUND TECHNOLOGY

Prior known methods for synthesizing the aforesaid aminosugars include, for example, (1) those which use sugars as starting materials [see, for example, Topics in Antibiotic Chemistry, Ellis Horwood, Ltd., Chichester, Vol. 2, pages 137–155 and Chem. Comm., 973 (1976)]; (2) those which comprise using petrochemical products as starting materials, subjecting them to stereoselective transformation to obtain the desired products as racemic mixtures [Angew. Chem, 90, 728 (1978) and Bull. Chem. Soc. Jpn., 52, 2731 (1979)]; and (3) those which use optically active naturally occurring materials other than sugars as starting materials [see, for example, Tetrahedron Letters, No. 40, pp. 3883–3886 (1979); ibid., 21, 2999 (1980); ibid., 22, 4017, 5073 (1981); and J. Chem. Soc. Chem. Comm., 442 (1980)]. The methods (1) are advantageous for obtaining optically active compounds because they start from sugars which already have a chiral center. But with these methods, the desired products cannot be obtained unless they go through long steps and therefore, these methods are economically disadvantageous. The key point of the methods (2) is the stereoselective transformation. But no decisive method is available for performing the stereoselective reaction, and another problem is that the final compounds should be optically resolved. At present, the methods (3) seem to be most advantageous for practical purposes. (+)Tartaric acid and D-threonine have been used as starting materials in the methods (3). But when tartaric acid is used as a starting material, the same defect as mentioned with regard to the methods (1) exists. Furthermore, D-threonine itself is not easy to synthesize because its synthesis requires a multiplicity of steps.

DISCLOSURE OF THE INVENTION

The present inventors fully considered the foregoing technical background, and discovered that the compounds of formula (I) which can be derived, for example, from (−)lactate esters or (+)lactate esters are important intermediates which can be easily converted to daunosamine, acosamine, ristosamine, or enantiomers thereof. This discovery has led to the present invention.

The term "lower", used in the present specification and the appended claims, means that a compound or group qualified by this term has not more than 4, preferably not more than 2, carbon atoms.

The "alkyl group" which is represented by R and R' in formula (I) is a linear or branched saturated aliphatic hydrocarbon group, and includes, for example, methyl, ethyl, propyl, isopropyl, butyl, isobutyl, t-butyl, pentyl, isoamyl and heptyl. Lower alkyl groups are preferred. Examples of the "aryl group" are phenyl, tolyl and naphthyl, phenyl being preferred. The "alkylene group" which can be formed by R and R' may be linear or branched, and preferably has 5 to 12 carbon atoms. Specific examples include hexylene, heptylene, octylene and dodecylene.

On the other hand, the "lower alkyl group" represented by $R^1$ and $R^2$ may also be either linear or branched, and includes, for example, methyl, ethyl, propyl, isopropyl, butyl, isobutyl, t-butyl and pentyl. $R^1$ is preferably methyl.

The "acyl group" which can be represented by $R^2$ is a monovalent group resulting from the removal of OH from the carboxyl group of a carboxylic acid, and includes, for example, acetyl, propionyl, butyryl, phenylacetyl, benzoyl, p-chlorobenzoyl, chloroacetyl, dichloroacetyl, trichloroacetyl, and trifluoroacetyl. Lower alkanoyl groups such as acetyl and propionyl and lower haloalkanoyl groups such as trifluoroacetyl are preferred.

The compounds of formula (I) have two a symmetric carbon atoms asterisked in the above formula (I). The stereochemistry at these asymmetric carbon atoms may be an S- or R-configuration. The compounds of formula (I) can exist as optically active compounds or as a diastereomeric mixture (or a racemic mixture).

Typical specific examples of the compounds of formula (I) include
ethyl (4S, 5S)-3-amino-4,5-(cyclohexylidenedioxy)-2-hexenoate,
t-butyl (4S, 5S)-3-amino-4,5-(cyclohexylidenedioxy)-2-hexenoate,
ethyl (4S, 5S)-3-amino-4,5-(cyclododecylidenedioxy)-2-hexenoate,
t-butyl (4S, 5S)-3-amino-4,5-(cyclododecylidenedioxy)-2-hexenoate,
ethyl (4S, 5S)-3-amino-4,5-(cyclopentylidenedioxy)-2-hexenoate,
t-butyl (4S, 5S)-3-amino-4,5-(cyclopentylidenedioxy)-2-hexenoate,
ethyl (4S, 5S)-3-amino-4,5-(diphenylmethylenedioxy)-2hexenoate,
t-butyl (4S, 5S)-3-amino-4,5-(diphenylmethylenedioxy)-2-hexenoate,
ethyl (4S, 5S)-3-amino-4,5-(2,2-propylidenedioxy)-2-hexenoate,
t-butyl (4S, 5S)-3-amino-4,5-(2,2-propylidenedioxy)-2-hexenoate,
ethyl (4S, 5S)-3-amino-4,5-(3,3-pentylidenedioxy)-2-hexenoate, t-butyl (4S, 5S)-3-amino-4,5-(3,3-pentylidenedioxy)-2-hexenoate,
(4R, 5S) derivatives of the foregoing compounds, and compounds obtained by acetylating, benzoylating or trifluoroacetylating the 3-amino groups of the foregoing compounds.

According to this invention, the compounds of formula (I) can be produced from lactic acid derivatives of formula (IV) below through the route schematically shown below.

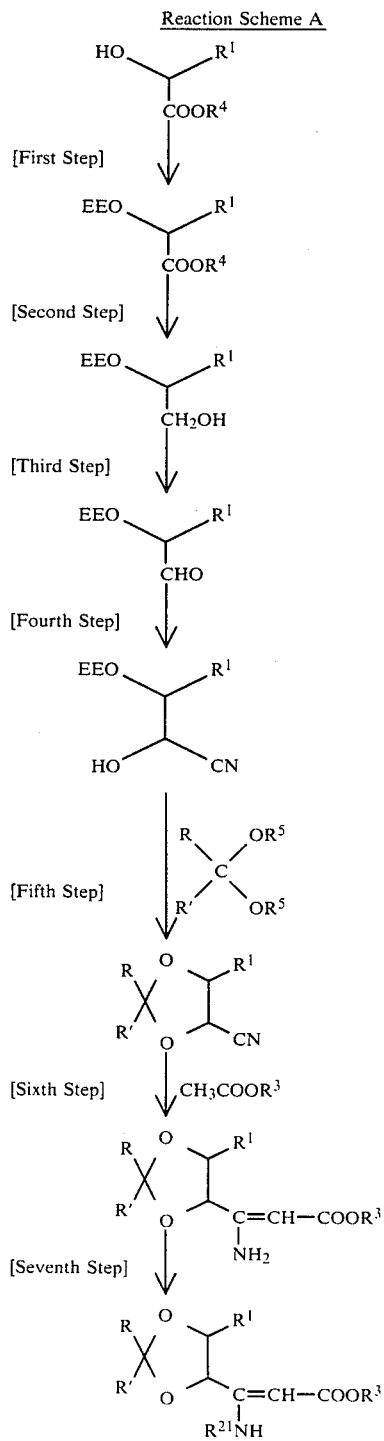

In the above formulae, $R^4$ and $R^5$ each represent a lower alkyl group; EE represents an ethoxyethyl group; $R^{21}$ represents an acyl group; and R, R', $R^1$ and $R^3$ are as defined above.

[First Step]

This step comprises reacting the lactic acid derivative of general formula (IV) with ethyl vinyl ether to protect the hydroxyl group of lactic acid with an ethoxyethyl group and obtain a compound of general formula (V). Advantageously, this step can be carried out in the presence of an acid catalyst. Examples of such an acid catalyst include mineral acids such as hydrochloric acid, sulfuric acid and phosphoric acid, and organic acids such as p-toluenesulfonic acid, camphorsulfonic acid, pyridinium p-toluenesulfonate, and bis(trimethylsilyl)sulfate. It is sufficient that these acid catalysts are used in a so-called catalytic amount.

The above reaction is carried out generally in a solvent. Examples of usable solvents include dichloromethane, dichloroethane, chloroform, carbon tetrachloride, benzene, hexane and ether. The reaction can be carried out usually at $-30°$ C. to the boiling point of the solvent.

[Second Step]

This step comprises reducing the compound of general formula (V) formed in the first step with a metal hydride to produce an alcohol represented by general formula (VI).

Examples of the metal hydride which can be used as a reducing agent in this step are lithium aluminum hydride, diisobutyl aluminum and lithium borohydride.

In performing this step, the reduction can be carried out generally in an inert solvent, for example dichloromethane or an ether-type solvent such as diethyl ether or tetrahydrofuran. The reduction proceeds smoothly at a temperature in the range of from 0° C. to the boiling point of the solvent.

[Third Step]

This step comprises oxidizing the alcohol represented by general formula (VI) to produce an aldehyde represented by general formula (VII).

The oxidation can be carried out in a customary manner in the presence of an oxidizing agent. As the oxidizing agent, there can be used, for example, chromic anhydride, an oxygen-containing gas, and dimethyl sulfoxide. Dimethyl sulfoxide is preferred among them. In using the oxidizing agent, it is advantageous to use together an oxidation promoter such as oxalyl chloride or a pyridine/sulfur trioxide complex. Usually, the promoter is used in an amount nearly equal to dimethyl sulfoxide.

Dichloromethane is most suitable as a solvent for the above reaction, but dichloroethane and chloroform can also be used. The reaction can be carried out at a temperature in the range of $-100°$ C. to 100° C., but from the standpoint of efficiency and operational simplicity, temperatures from $-78°$ C. to room temperature are preferred.

[Fourth Step]

This step comprises reacting the aldehyde represented by general formula (VII) with a cyano-containing compound to produce a cyanohydrin represented by general formula (II).

As the cyano-containing compound which can be reacted with the compound of formula (VII), there can be used, for example, hydrogen cyanide, trimethylsilyl cyanide, acetonecyanohydrin, diethyl aluminum cyanide, and sodium cyanide/sulfuric acid. From the standpoint of safety, acetonecyanohydrin is especially preferably used.

The use of a solvent is not particularly necessary. If necessary, aprotic solvents such as acetone, dichloromethane, hexane and benzene can be used. The reaction can generally be carried out at a temperature in the range of −78° C. to 100° C. Usually, the reaction proceeds fully smoothly at room temperature.

[Fifth Step]

This step comprises reacting the cyanohydrin represented by general formula (VIII) with a ketone dialkyl acetal of general formula (IX) to produce a 2,3-(alkylidenedioxy)butanenitrile represented by general formula (II).

The ketone dialkylacetals represented by general formula (III) are known compounds which are easily available industrially. For example, acetone dimethyl acetal, cyclohexanone dimethyl acetal, cyclohexanone diethyl acetal, benzophenone dimethyl acetal, cyclododecanone dimethyl acetal and diethylketone diethyl acetal can be used.

Advantageously, the above reaction can be carried out in the presence of an acid catalyst. Examples of usable acid catalysts include mineral acids such a hydrochloric acid, sulfuric acid and phosphoric acid, and organic acids such as p-toluenesulfonic acid, camphorsulfonic acid, pyridinium p-toluenesulfonate and bistrimethylsillyl sulfate. The amount of the acid catalyst used is not strict, and a so-called catalytic amount is sufficient.

Preferably, a solvent is used in carrying out the present reaction, and there can be suitably used aprotic solvents such as ether, dichloromethane, chloroform, dichloroethane, benzene, hexane, pentane and tetrahydrofuran. The reaction temperature is not critical, but generally, temperatures between 0° C. and the boiling point of the solvent can be advantageously used.

The amount of the acetal of formula (IX) to the compound of formula (VIII) is neither critical. Generally, it is convenient to use 1 to 1.5 moles of the compound of formula (IX) per mole of the compound of formula (VIII).

In the present invention, an alcohol is formed as a by-product. By removing the alcohol during the reaction, the desired final compound of formula (II) can be obtained efficiently. The by-product alcohol can be removed, for example, by utilizing the Dien-Stark's device or by adsorption on molecular sieves, etc.

The resulting compound of formula (II), as required, may be easily separated into optically active compounds having a (2S, 3S)-configuration and a (2R, 3S)-configuration and purified by means known per se such as column chromatography. Examples of the compound of general formula (II) which can be so obtained include 2,3-cyclohexylidenedioxybutanenitrile, 2,3-cyclopentylidenedioxybutanenitrile, 2,3-cyclododecylidenedioxybutanenitrile, 2,3-(2,2-propylidenedioxy)butanenitrile, 2,3-(3,3-pentylidenedioxy)butanenitrile, 2,3-(diphenylmethylenedioxy)butanenitrile, and 2,3-(cyclohexylidenedioxy)pentanenitrile.

[Sixth Step]

This step comprises reacting the compound of general formula (II) with an acetic acid ester of general formula (III) to produce a β-aminoacrylic acid derivative of the invention represented by formula (Ia).

The acetic acid ester of formula (III) which is reacted with the compound of formula (II) is easily available as an industrial material. Examples include methyl acetate, ethyl acetate, propyl acetate, isobutyl acetate, t-butyl acetate and t-amyl acetate.

Advantageously, the reaction of the compound of formula (II) with the acetic acid ester of formula (III) is carried out in the presence of a base. The base can be directly added to the reaction system. In order to obtain the β-aminoacrylic acid derivative of formula (Ia) efficiently by the present reaction, it is preferred to react the acetic acid ester of formula (III) in advance with a base and then react the resulting product with the compound of formula (II).

Bases which can be used are, for example, metal amides such as Mg[N(C₂H₅)₂]₂, Mg[N(iso-C₃H₇)₂]₂,

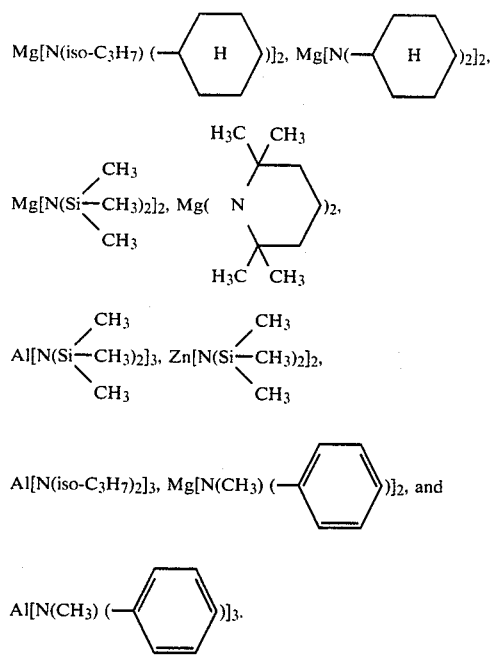

The above base can be used generally in a proportion of 1 to 5 equivalents, preferably 1.5 to 2.5 equivalents, per mole of the acetic acid ester of general formula (III).

Advantageously, the above reaction can be carried out in a solvent. There can, for example, be used an aprotic solvent such as toluene, hexane, diethyl ether, or tetrahydrofuran. Above all, diethyl ether is preferred in view of the efficiency and economy of the reaction. There is no particular restriction on the reaction temperature. The suitable temperature is generally −100° C. to 50° C., preferably −78° C. to 0° C.

The amount of the acetic acid ester of formula (III) to the compound of formula (II) is neither critical, and can be varied over a broad range. Generally, the acetic acid ester of formula (III) is conveniently used in an amount of 1 to 10 moles, preferably 2 to 4 moles, per mole of the compound of formula (II). compound of formula (II).

[Seventh Step]

This step comprises acylating the β-aminoacrylic acid derivative of general formula (Ia) obtained in the sixth step to produce the β-acylaminoacrylic acid derivative of this invention represented by general formula (Ib).

Examples of suitable acylating agents for use in the acylation of this step include anhydrides and halides of lower alkanoic acids such as acetic acid or propionic acid; anhydrides and halides of lower haloalkanoic acids such as trifluoroacetic acid, trichloroacetic acid, monochloroacetic acid, monofluoroacetic acid and monobromoacetic acid; and anhydrides and halides of aromatic carboxylic acids such as benzoic acid and fumaric acid.

The acylation can be carried out by any methods known per se with regard to the acylation of amino groups. For good efficiency, this reaction is carried out preferably in the presence of a base. Examples of usable bases are tertiary amines such as triethylamine, diisopropylethylamine, pyridine, quinoline, 4-dimethylaminopyridine and N,N-dimethylaniline, and sodium or potassium salts of carboxylic acids which are used as acylating agents. The amount of the base used is not critical. Generally, it is conveniently 1 to 10 moles, preferably 1.1 to 3 moles, per mole of the compound of formula (Ia).

The acylation reaction does not always require the use of a solvent. But the reaction may be carried out in a solvent which is not directly involved in the reaction, such as toluene, benzene, hexane, diethyl ether, tetrahydrofuran, or dichloromethane.

The reaction temperature is not critical. The suitable temperature is generally −78° C. to 100° C., preferably 0° to 80° C.

The amount of the acylating agent used relative to the compound of formula (Ia) is not critical, and can be varied over a wide range depending upon, for example, the type of the acylating agent. Generally, it is desirable to use an equimolar proportion to a very large excess of the acylating agent, preferably 1.1 to 5 moles of the acylating agent per mole of the compound of general formula (Ia).

The compound of this invention represented by general formula (Ia) or (Ib) produced as described above can be isolated and purified by methods known per se, such as distillation, extraction, recrystallization, and chromatography.

BEST MODE OF WORKING THE INVENTION

The following Examples illustrate the present invention more specifically.

EXAMPLE 1

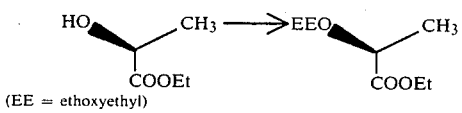
(EE = ethoxyethyl)

S(−)Ethyl lactate (11.8 g, 0.1 mole) and ethyl vinyl ether (10.8 g, 14.3 ml, 0.15 mole) were dissolved in dichloromethane (100 ml). A solution of pyridinium p-toluenesulfonate (1.53 g, 6 mmoles) in dichloromethane (26 ml) was slowly added at 0° C. to the resulting solution. The mixture was stirred at 0° C. for 50 minutes and then at room temperature for 1 hour, and washed with a saturated aqueous solution of sodium chloride. The aqueous layer was extracted with ether. The organic layer was dried over anhydrous sodium sulfate and then concentrated and distilled to give ethyl (2S)-2-(1-ethoxy)ethoxypropanoate (18.4 g, yield 97%).

Boiling point: 77°–78° C./26 torr.

$^1$H NMR (CDCl$_3$): δ 1.1–1.5 (m, 12H), 3.3–3.9 (m, 2H), 4.20 (q, 2H, J=7.5 Hz), 4.30 (q, 1H, J=6.0 Hz), 4.76 (q, 1H, J=6.0 Hz).

$[\alpha]_D^{28}$: −71.7° (MeOH, c 4.18).

EXAMPLE 2

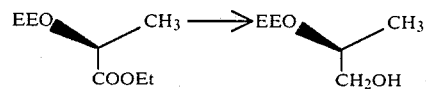

Lithium aluminum hydride (4.05 g, 0.106 mole) was suspended and dissolved in ether (150 ml), and with vigorous stirring, a solution of the starting compound (14.9 g, 0.078 mole) obtained in Example 1 in ether (100 ml) was addded to the solution at 0° C. over the course of 25 minutes. Subsequently, the mixture was heated under reflux for 7 hours, and cooled. The excess of the hydride was decomposed with a saturated aqueous solution of sodium sulfate, and the precipitated inorganic material was separated by filtration on a Celite layer. The filtrate was concentrated and distilled to give the desired alcohol (10.9 g, yield 94%).

Boiling point: 77°–79° C./17 torr.

$^1$H NMR (CDCl$_3$): δ 1.1–1.4 (m, 9H), 3.1–4.0 (m, 5H), 4.70 and 4.78 (2q, each J=5.3 Hz, 1H).

Elemental analysis for C$_7$H$_{16}$O$_3$: Calculated (%): C, 56.73; H, 10.88. Found (%): C, 56.91; H, 11.03.

$[D]_D^{29}$: +42.2° (CHCl$_3$, c 5.87).

EXAMPLE 3

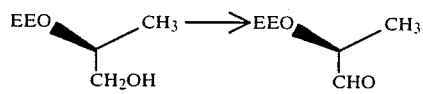

Oxalyl chloride (6.4 g, 4.4 ml, 0.050 mole) was dissolved in dichloromethane (100 ml), and a solution of dimethyl sulfoxide (7.9 g, 7.2 ml, 0.1 mole) in dichloromethane (40 ml) was added to this solution at −70° C. over the course of 15 minutes. The mixture was stirred at the same temperature for 10 minutes, and then a solution of the alcohol (5.0 g, 0.034 mole) obtained in Example 2 in dichloromethane (50 ml) was added dropwise over the course of 15 minutes. The temperature of the reaction solution was maintained at −65° to −70° C. It was stirred for 30 minutes at −70° C., and triethylamine (17.1 g, 23.5 ml, 0.168 mole) was added over the course of 15 minutes. The mixture was stirred at the same temperature for 25 minutes. The cold bath was then removed, and the temperature was gradually raised to 10° C. The reaction mixture was work-up, and distillation gave the desired aldehyde (3.82 g, yield 78%).

$^1$H NMR (CDCl$_3$): δ 1.1–1.4 (m, 9H), 3.20 (q, J=7.5 Hz, 2H), 3.7–4.3 (m, 1H), 4.71 and 4.81 (q, J=5.3 Hz, 1H), 9.59 and 9.64 (d, J=3.0 Hz and 1.5 Hz respectively, 1H).

$[\alpha]_D^{23}$: −56.9° (CHCl$_3$, c 6.31).

EXAMPLE 4

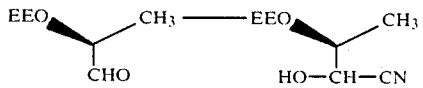

The aldehyde (2.2 g, 15 mmoles) obtained in Example 3, acetone cyanohydrin (1.53 g, 1.64 ml, 18 mmoles) and triethylamine (0.021 ml) were stirred at 0° C. for 1 hour. The low-boiling materials were evaporated under reduced pressure, and the residue was purified by silica gel column chromatography (hexane-ethyl acetate=3:1-1:1) to give the desired cyanohydrin (2.6 g, yield 100%).

Rf: 0.28 (hexane-ethyl acetate=3:1)

$^1$H NMR (CDCl$_3$): δ 1.1–1.4 (m, 9H), 3.4–4.1 (m, 3H), 4.25 and 4.28 (2d, J=1.5 Hz and 4.5 Hz respectively, 1H in total), 4.6–5.0 (m, 1H).

EXAMPLE 5

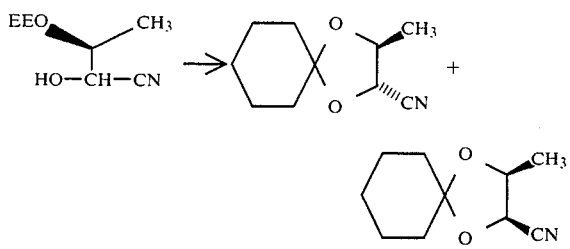

A dichloromethane solution (1 mole/dm$^3$, 0.45 ml) of bis(trimethylsilyl)sulfate was added at 0° C. to a solution of the cyanohydrin (2.55 g, 14.7 mmoles) obtained in Example 4 and cyclohexanone dimethyl acetal (2.39 g, 16.5 mmoles) in the presence of Molecular Sieve 4A (about 5 g), and the mixture was stirred at 0° C. for 10 minutes and then at room temperature for 30 minutes. Pyridine (0.1 ml) was added, and then the insoluble material was separated by filtration. The filtrate was concentrated, and the residue was purified by column chromatography (hexane-ethyl acetate=10:1–6:1). The first fraction was (2S, 3S)-2,3-cyclohexylidenedioxybutanenitrile (0.69 g, yield 28%).

Rf: 0.68 (SiO$_2$ TLC, hexane-ethyl acetate=3:1).

Boiling point: 130°–155° C. (bath temperature)/16 torr.

$^1$H NMR (CCl$_4$): δ 1.38 (d, J=6.0 Hz, 3H), 1.5–1.8 (m, 10H), 4.02 (d, J=7.5 Hz, 1H), 4.36 (quintet, J=6.0 Hz, 1H).

MS: m/z (relative intensity) 181 (M$^+$, 9.3), 152 (11), 138 (100), 55 (29), 41 (15).

Elemental analysis for C$_{10}$H$_{15}$NO$_2$: Calculated (%): C, 66.27; H, 8.34; N, 7.73. Found (%): C, 66.38; H, 8.39; N, 7.57.

$[α]_D^{24}$: +15.5° (CHCl$_3$, c 8.84).

The next fraction was (2R, 3S)-2,3-cyclohexylidenedioxybutanenitrile (1.05 g, yield 40%).

Rf: 0.55 (SiO$_2$, hexane-ethyl acetate=3:1).

Boiling point: 130°–155° C. (bath temperature)/16 torr.

$^1$H NMR (CCl$_4$): δ 1.45 (d, J=6.0 Hz, 3H), 1.5–1.8 (m, 10H), 4.21 (quintet, J=6.0 Hz), 4.58 (d, J=5.3 Hz, 1H).

MS: m/z (relative intensity) 181 (M$^+$, 9.3), 1.52 (12), 138 (100), 84 (10), 55 (31), 42 (10), 41 (15).

Elemental analysis for C$_{10}$H$_{15}$NO$_2$: Calculated (%): C, 66.27; H, 8.34; N, 7.73 Found (%): C, 66.40; H, 8.44; N, 8.09

$[α]_D^{23}$: +26.4° (CHCl$_3$, c 5.57).

The (2S, 3S)- and (2R, 3S)-2,3-cyclohexylidenedioxybutanenitriles were found to have an optical purity, measured by using a shift reagent [Eu(TFC)$_3$], of more than 95%.

EXAMPLES 6 TO 9

(±)-Cyanohydrin was obtained from (±)-methyl lactate as a starting material in the same way as in Examples 1 to 4. The (±)cyanohydrin was reacted with each of the various acetals of formula (IX) in the same way as in Example 5 to obtain products represented by (2S*, S*)-(II-1) and (2R*, 3S*)-(II-1). The results and the spectral data of the products are shown in Table 1 below.

TABLE 1

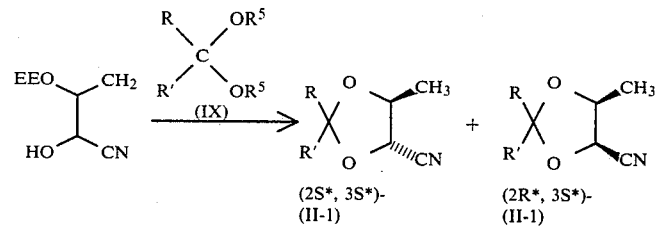

| Example | Compound of formula (IX) | Yield (%) (2S*, 3S*)-(II-1): (2R*, 3S*)-(II-1) | Physical properties | |
|---|---|---|---|---|
| | | | (2S*, 3S*)-(II-1) | (2R*, 3S*)-(II-1) |
| 6 | ⬡OMe OMe | 71 (40:60) | Same as in Example 1 | |
| 7 | Me$_2$C(OMe)$_2$ | 60 (42:58) | Rf 0.73 (ethyl acetate: hexane = 1:3) b.p. 100° C./14 torr $^1$H NMR (CDCl$_3$): δ 1.40 (d, J = 6Hz, 3H), 1,52 (s, 6H), 4.13 (d, J = 7Hz 1H), 4.46 (quintet, J = 6Hz, 1H). | Rf 0.6 (ethyl acetate: hexane = 1:3) b.p. 100° C./14 torr $^1$H NMR (CDCl$_3$): δ 1.38 (s, 3H), 1.52 (d, J = 6Hz, 3H), 1.56 (s, 3H), 4.32 (quintet, J = 6Hz, 1H), 4.70 (d, J = 5Hz, 1H). |

TABLE 1-continued

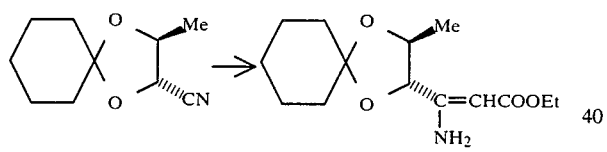

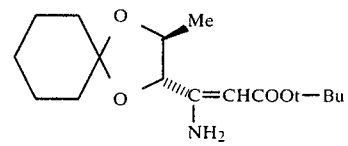

| Example | Compound of formula (IX) | Yield (%) (2S*, 3S*)-(II-1): (2R*, 3S*)-(II-1) | Physical properties (2S*, 3S*)-(II-1) | (2R*, 3S*)-(II-1) |
|---|---|---|---|---|
| 8 | $(CH_2)_{11}$  $C(OMe)_2$ | 67 (37:63) | Rf 0.64 (ethyl acetate: hexane = 1:3) m.p. 61–64° C. $^1$H NMR (CDCl$_3$): δ 1.2–2.1 (m, 25H), 4.15 (d, J = 7Hz, 1H), 4.43 (q, J = 6Hz, 1H). | Rf 0.53 (ethyl acetate: hexane = 1:3) m.p. 73–75° C. $^1$H NMR (CDCl$_3$): δ 1.0–1.9 (m, 25H), 4.30 (q, J = 6Hz, 1H), 4.70 (d, J = 5Hz, 1H). |
| 9 | Ph$_2$C(OMe)$_2$ | 63 (45:55) | Rf 0.51 (ethyl acetate: hexane = 3:1) m.p. 68–69° C. $^1$H NMR (CDCl$_3$): δ 1.48 (d, J = 5Hz, 3H), 4.37 and 4.25–4.45 (d, J = 4Hz and m, 2H in total), 7.2–7.7 (m, 10H). | Rf 0.44 (ethyl acetate: hexane = 3:1) m.p. 54.4–56° C. $^1$H NMR (CDCl$_3$): δ 1.60 (d, J = 6Hz, 3H), 4.30 (quintet, J = 6Hz, 1H), 4.86 (d, J = 6Hz, 1H), 7.2–7.7 (m, 10H). |

Me = methyl.
Ph = phenyl

EXAMPLE 10

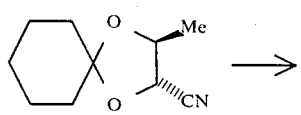

Diisopropylamine (2.84 g, 28 mmoles) was added to an ethereal solution (21 ml) of ethyl magnesium bromide (14 mmoles) with ice cooling, and the mixture was stirred for 1.5 hours to prepare Mg[N(iso-C$_3$H$_7$)$_2$]$_2$. The solution was cooled to −78° C., and ethyl acetate (617 mg, 7 mmoles) and then (2S*, 3S*)-2,3-cyclohexylidenedioxybutanenitrile (370 mg, 1.75 mmoles) were added. The reaction temperature was gradually raised to 0° C. over the course of about 2 hours. An aqueous solution of ammonium chloride was added, and the reaction was stopped. The reaction mixture was extracted with ether. The extract was dried, concentrated and distilled to isolate ethyl (4S*, 5S*)-3-amino-4,5-(cyclohexylidenedioxy)-2-hexenoate (370 mg, yield 79%).

Boiling point: 116° C./0.09 torr.

$^1$H NMR (CDCl$_3$): δ 1.26, 1.35 and 1.64 (t, d and br. s respectively, 16H in total), 3.8–4.3 and 4.14 (m and q respectively, 4H in total), 4.54 (s, 1H), 5.8–7.4 (br, 2H).

EXAMPLE 11

Diisoprpylamine (2.84 g, 28 mmoles) was added to an ethereal solution (21 ml) of ethyl magnesium bromide (14 mmoles) with ice cooling, and the mixture was stirred for 1 hour. Then, t-butyl acetate (813 mg, 7 mmoles) was added. The mixture was stirred at the same temperature for 30 minutes. Subsequently, (2S*, 3S*)-2,3-cyclohexylidenedioxybutanenitrile (634 mg, 3.5 mmoles) was added, and the mixture was stirred further for 3 hours. An aqueous solution of ammonium chloride was added and the reaction was stopped. The reaction mixture was extracted with ether. The extract was dried, concentrated, and distilled to isolate t-butyl (4S*, 5S*)-3-amino-4,5-(cyclohexylidenedioxy)-2-hexenoate (790 mg, yield 76%).

Boiling point: 128° C./0.07 torr.

Melting point: 96°–97° C.

$^1$H NMR (CDCl$_3$): δ 1.33 (d, 3H), 1.46 (s, 9H), 1.63 (br, 10H), 3.7–4.0 (m, 2H), 4.43 (s, 1H), 5.9–6.9 (br, 2H).

EXAMPLES 12 TO 15

The compounds of Examples 12 and 13 shown in Table 2 were synthesized under the same conditions as in Example 10. The compounds of Examples 14 and 15 in Table 2 were synthesized under the same conditions as in Example 11.

TABLE 2

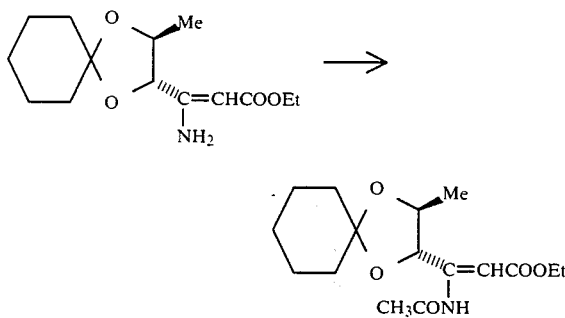

(II-1) → (Ia-1)

| Example | R | R' | Steric configuration of the 2-position of (II-1) | R³ | Yield (%) | Boiling point [or Rf (SiO₂)] | ¹H NMR |
|---|---|---|---|---|---|---|---|
| 12 | Me | Me | S* | Et | 59 | 92° C./0.3 torr | (CCl₄), δ1.22, 1.33 and 1.40 (t, d and s respectively, 12H in total), 3.7–3.9 (m, 2H), 4.01 (q, 2H), 4.36 (s, 1H), 5.4–7.1 (br, 2H). |
| 13 | Ph | Ph | S* | Et | 63 | 0.75 (ethyl acetate-hexane = 1:3) | (CDCl₃), δ1.20 (t, 3H), 1.42 (d, 3H), 4.1–4.3 (m, 2H), 4.50 (s, 1H), 7.1–7.7 (m, 12H). |
| 14 | Me | Me | S* | t-Bu | 85 | 133° C./0.6 torr | (CDCl₃), δ1.35 (d, 3H), 1.44 and 1.47 (2s, 15H in total), 3.7–4.0 (m, 2H), 4.43 (s, 1H), 5.7–6.7 (br, 2H). |
| 15 | —(CH₂)₅— | | R* | t-Bu | 75 | 124° C./0.007 torr | (CCl₄), δ1.23 (d, 3H), 1.42 (s, 9H), 1.59 and 1.67 (2br, s, 10H in total), 4.2–4.4 (m, 3H), 6.1–6.8 (br, 2H). |

Me = methyl, Et = ethyl, t-Bu = t-butyl, Ph = phenyl

EXAMPLE 16

A mixture of ethyl (4S*, 5S*)-3-amino-4,5-(cyclohexylidenedioxy)-2-hexenoate (300 mg, 1.12 mmoles), acetic anhydride (3 ml) and sodium acetate (98 mg, 1.2 mmoles) was heated overnight with stirring at 80° C. The excess of acetic anhydride and the by-product acetic acid were removed under reduced pressure. The residue was poured into water and extracted with ether. The extract was concentrated and subjected to TLC to isolate ethyl (4S*, 5S*)-3-acetamido-4,5-(cyclohexylidenedioxy)-2-hexenoate (219 mg, yield 63%).

Rf: 0.43 (hexane-ethyl acetate = 5:1).

¹H NMR (CCl₄): δ 1.30, 1.34 and 1.62 (t, d and br. s respectively, 16H in total), 2.10 (s, 3H), 3.86 and 4.11 (quintet and q respectively, 3H in total), 5.45 (d,1H), 5.53 (s, 1H), 11.06 (broad, 1H).

EXAMPLES 17 TO 23

The compounds shown in Table 3 were synthesized under the same conditions as in Example 16.

TABLE 3

(Ia-1) → (Ib-1)

| Example | R | R' | Steric configuration of the 4-position of (Ia-1) | R³ | Acylating agent | R²¹ | Yield (%) | Rf (SiO₂) | ¹H NMR |
|---|---|---|---|---|---|---|---|---|---|
| 17 | —(CH₂)₅— | | R* | t-Bu | Ac₂O, Py | Ac | 64 | 0.62 (hexane-ethyl acetate=3:1) | (CCl₄), δ 1.03 (d, 3H), 1.44 and 1.3–1.7 (s and br respec-, tively, 9H in total), 2.08 (s, 3H), 4.59 (quintet, 1H), 5.36 (s, 1H), 5.59 (d, 1H), 10.32 (br, 1H). |
| 18 | —(CH₂)₅— | | S* | t-Bu | Ac₂O, Py | Ac | 74 | 0.63 (hexane-ethyl | (CCl₄), δ 1.32 (d, 3H), 1.47 (s, 9H), |

TABLE 3-continued $$\underset{(Ia-1)}{\overset{R}{\underset{R'}{\times}}\overset{O}{\underset{O}{\bigg]}}\overset{Me}{\underset{\underset{NH_2}{|}}{C=CHCOOR^3}}} \longrightarrow \underset{(Ib-1)}{\overset{R}{\underset{R'}{\times}}\overset{O}{\underset{O}{\bigg]}}\overset{Me}{\underset{\underset{R^{21}NH}{|}}{C=CHCOOR^3}}}$$

| Example | R | R' | Steric configuration of the 4-position of (Ia-1) | $R^3$ | Acylating agent | $R^{21}$ | Yield (%) | Rf (SiO$_2$) | $^1$H NMR |
|---|---|---|---|---|---|---|---|---|---|
| | | | | | | | | acetate=3:1) | 1.6 (br, 10H), 2.07 (s, 3H), 4.83 (quintet, 1H), 5.41 and 5.47 (s and d, 2H in total), 1.11 (br, 1H). |
| 19 | —(CH$_2$)$_5$— | | S* | Et | (CF$_3$CO)$_2$O, CF$_3$CO$_2$Na | CF$_3$CO | 22 | 0.63 (hexane-ethyl acetate=3:1) | (CDCl$_3$), δ 1.31, 1.40 and 1.66 (t, d and br, 16H in total), 3.8–4.3 (m, 3H), 5.3–5.7 (m, 1H), 5.91 (s, 1H), 12.1 (br, 1H). |
| 20 | Me | Me | S* | t-Bu | Ac$_2$O, Py | Ac | 73 | 0.60 (hexane-ethyl acetate=3:1) | (CDCl$_3$), δ 1.41, 1.46 and 1.49 (d, s and d, 18H in total), 2.13 (s, 3H), 3.90 (quintet, 1H), 5.53 and 5.57 (s and d, 2H in total), 11.1 (br, 1H). |
| 21 | Me | Me | S* | Et | Ac$_2$O, Py | Ac | 53 | 0.57 (hexane-ethyl acetate=3:1) | (CCl$_4$), δ 1.26, 1.31 and 1.39 (t, d, and s respectively, 12H in total), 2.06 (s, 3H), 4.01 (quintet, 1H), 5.40 and 5.46 (d and s, 2H in total), 11.1 (br, 1H). |
| 22 | Ph | Ph | S* | Et | Ac$_2$O, Py | Ac | 41 | 0.30 (hexane-ethyl acetate=5:1) | (CDCl$_3$), δ 1.20 and 1.29 (t and d, 6H in total), 1.76 (s, 3H), 3.9–4.4 (m, 3H), 5.39 (s, 1H), 5.73 (d, 1H), 7.2–7.7 (m, 10H), 11.0 (br, 1H). |
| 23 | —(CH$_2$)$_{11}$— | | S* | Et | Ac$_2$O, Py | Ac | 23 (total yield from the nitrile compound) | 0.49 (hexane-ethyl acetate=5:1) | (CDCl$_3$), δ 1.1–1.8, (m, 28H), 2.13 (s, 3H), 3.87 (quintet, 1H), 4.17 (q, 2H), 5.61 and 5.65 (d and s, 2H in total), 1.09 (br, 1H). |

Ac = CH$_3$CO,
Py = pyridine

UTILIZABILITY IN INDUSTRY

The compounds of formula (I) provided by this invention are useful as intermediates for the synthesis of medicines, particularly intermediates for the synthesis of amino sugars such as daunosamine (which is the sugar moiety of daunomycin useful as an anti-cancer agent), 3-epi.daunosamine, acosamine and ristosamine. For example, the compound of formula (Ib) given hereinabove can be converted to an aminosugar through the route shown below schematically.

Reaction Scheme B

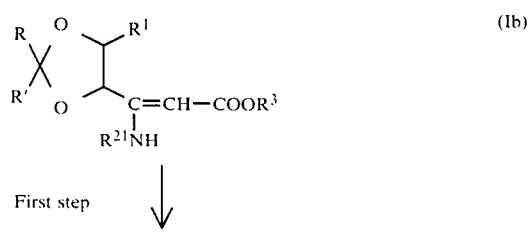

First step

-continued
Reaction Scheme B

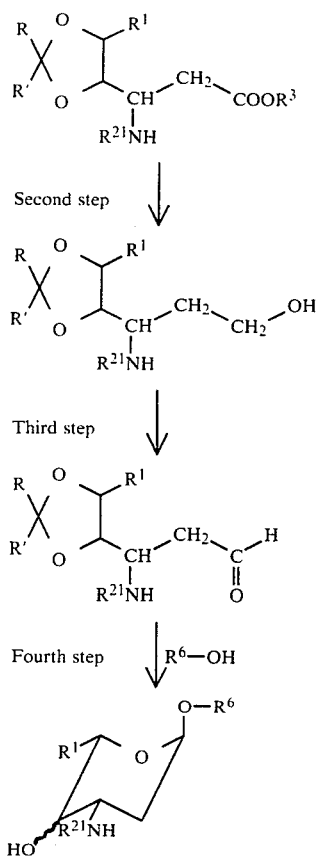

In the formulae, $R^6$ represents a hydrogen atom or a lower alkyl group, R, R', $R^1$, $R^{21}$ and $R^3$ are as defined hereinabove.

[First Step]

The β-acylaminoacrylic acid derivative of formula (Ib) is reduced to form a β-amino acid derivative of formula (X).

The reduction in this step can be achieved by hydrogenating the compound of formula (Ib) under atmospheric or elevated pressures. Hydrogenation in this step is carried out in the presence of a catalyst. Catalysts which can normally be used as hydrogenation catalysts of this kind may be employed in this invention. Examples include platinum oxide, palladium-carbon, rhodium-carbon, iridium-carbon and tris(triphenyl phosphine)rhodium chloride.

Desirably, this hydrogenation is carried out in a solvent, for example, water, methanol, ethanol, ethyl acetate, acetic acid, diethyl ether, cyclohexane, benzene, or mixtures of these. The reaction generally proceeds at room temperature to 100° C.

[Second Step]

The ester of formula (X) obtained in the first step is reduced to an alcohol of formula (XI).

The reduction in this step is carried out in the presence of a reducing agent, and for example, aluminum hydride, lithium aluminum hydride, lithium borohydride and isobutyl aluminum hydride can be used as the reducing agent.

This reaction can be carried out in a solvent. There may be used solvents which are not directly involved in the reaction, for example ether-type solvents such as diethyl ether, tetrahydrofuran and dimethoxyethane, dichloromethane, toluene, and hexane. Generally, the reaction proceeds smoothly at −78° C. to 100° C.

[Third Step]

In this step, the alcohol of formula (XI) obtained in the second step is oxidized in produce an aldehyde of formula (XII).

The oxidation in this step is carried out in the presence of an oxidizing agent. For example, a pyridine-chromic anhydride complex, pyridinium chlorochromate, pyridinium dichromate, and dimethyl sulfoxide may be used as the oxidizing agent.

Usually, the present reaction can be carried out in a solvent which is not directly involved in the reaction, such as dichloromethane, chloroform and diethyl ether.

Generally, the reaction proceeds smoothly at −78° C. to 100° C.

[Fourth Step]

In this step, the protective group in the aldehyde of formula (XII) is removed and the resulting compound is simultaneously cyclized. For this purpose, the compound (XII) is heated in water or a lower alcohol in the presence of a mineral acid such as hydrochloric acid and sulfuric acid or an organic acid such as acetic acid.

An amino sugar of formula (XIII) in which $R^6$ is H or a lower alkyl group depending upon the solvent used is obtained.

The reaction proceeds at room temperature to the refluxing temperature of the solvent.

The following Examples more specifically illustrate the synthesis of amino sugars from the compounds of formula (Ib).

EXAMPLE A

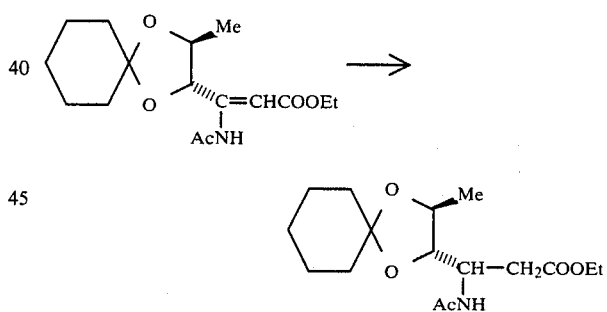

Ethyl (4S*, 5S*)-3-acetamido-4,5-(cyclohexylidenedioxy)-2-hexenoate (200 mg, 0.589 mmole) and platinum oxide (8 mg, 0.035 mmole) were heated in ethyl acetate (2 ml) with stirring in a hydrogen atmosphere (1 atm.) at 50° C. for 13 hours. The reaction mixture was filtered and concentrated. The residue was subjected to TLC, and ethyl (4S*, 5S*)-3-acetamido-4,5-(cyclohexylidenedioxy)hexanoate (163 mg, 81%) was isolated.

Rf: 0.14 (hexane-ethyl acetate: 3:1).

$^1$H NMR (diastereomer mixture) (CDCl$_3$): δ 1.25, 1.26 and 1.56 (d, s and br s respectively, 16H in total), 1.96 (s, 3H), 2.4–2.7 (m, 2H), 3.4–4.6 (m, 5H), 5.9–6.2 and 6.4–6.6 (2 br, d, 1H).

The ratio of the diasteromers was estimated at about 4:1 on the basis of gas chromatography and $^1$H NMR spectrum.

EXAMPLE B

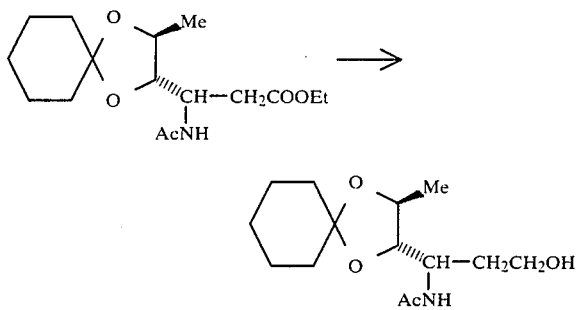

Lithium aluminum hydride (16.7 mg, 0.44 mmole) was dissolved in ether (3 ml) and the solution was cooled to 0° C. To the solution was added dropwise a solution of ethyl (4S*, 5S*)-3-acetamido-4,5-(cyclohexylidenedioxy)hexanoate (150 mg, 0.44 mmole) in ether (2 ml), and the mixture was stirred at the same temperature for 4.5 hours. Ether (20 ml) was added, and the excess of lithium aluminum hydride was decomposed with a small amount of saturated sodium sulfate. The excess of water was removed by anhydrous magnesium sulfate, and the residue was filtered through Celite and concentrated. TLC separation gave (4S*, 5S*)-3-acetamido-4,5-(cyclohexylidenedioxy)hexan-1-ol (103 mg, yield 86%).

Rf: 0.33 (ethyl acetate).

$^1$H NMR (diastereomer mixture) (CDCl$_3$): δ 1.36 (d, 3H), 1.63 (br s, 12H), 2.09 (s, 3H), 3.2–4.4 (m, 6H), 5.5–6.5 (br, 1H).

EXAMPLE C

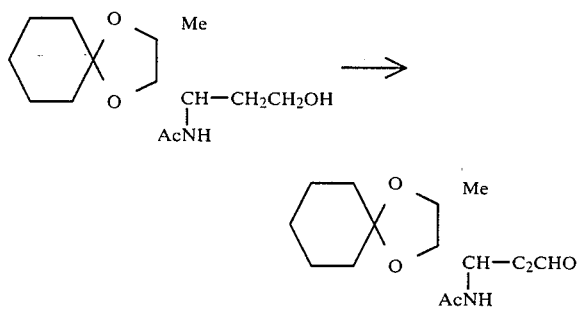

Oxalyl chloride (52.4 mg, 0.413 mmole) was dissolved in methylene chloride (2 ml), and the solution was cooled to −78° C. Dimethyl sulfoxide (70.3 mg, 0.9 mmole) was added, and the mixture was stirred for 15 minutes. A solution of (4S*, 5S*)-3-acetamido-4,5-(cyclohexylidenedioxy)hexan-1-ol (101 mg, 0.373 mmole) in dichloromethane (2 ml) was added. Fifteen minutes later, triethylamine (190 mg, 1.88 mmoles) was added, and the temperature was raised to room temperature. The reaction mixture was diluted with 20 ml of dichloromethane, washed with a saturated aqueous solution of sodium chloride, dried, and concentrated. TLC separation gave (4S*, 5S*)-3-acetamido-4,5-(cyclohexylidenedioxy)hexanal (82 mg, yield 82%).

Rf: 0.45 (ethyl acetate).

$^1$H NMR (diastereomer mixture) (CDCl$_3$): δ 1.30 (d, 3H), 1.58 (br s, 10H), 2.01 (s, 3H), 2.5–2.8 (m, 2H), 3.3–4.5 (m, 3H), 5.5–6.2 (2 br d, 1H), 9.86 (br s, 1H).

EXAMPLE D

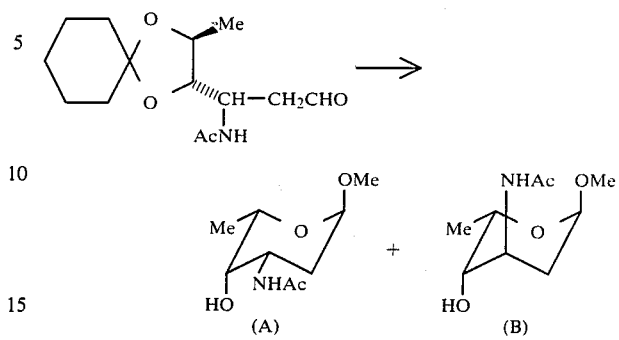

(4S*, 5S*)-3-acetamido-4,5-(cyclohexylidenedioxy)hexanal (70 mg, 0.26 mmole) was dissolved in methanol (3 ml), and hydrochloric acid was added to about 0.01N. The solution was stirred at room temperature for 6 hours and then neutralized with a small amount of sodium hydrogen carbonate. The precipitate was separated by filtration, and concentrated. The residue was subjected to TLC to isolate a mixture (37 mg, 70%) of (+)-N-acetyldaunosamine methyl ether (compound A) and (+)-3-epi-N-acetyldaunosamine methyl ether (compound B).

The ratio of A to B was found to be 18:82 by $^1$H NMR. Compound A agreed in TLC with that derived from an authentic sample.

Rf: 0.56 (acetone).

$^1$H NMR (CDCL$_3$): δ 1.22 and 1.31 (2d, J=7 Hz, 3H), 1.96, 2.15 and 1.8–2.4 (s, s and m respectively, 5H in total), 3.3–3.4 (4s, 3H in total), 3.6–4.4 (m, 3H), 4.75 and 5.06 (dd, both J=4 Hz, 2 Hz, 1H in total), 5.7–6.4 (br, 1H).

EXAMPLE E

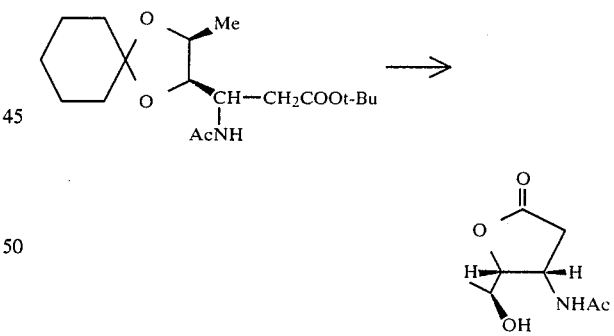

t-Butyl (4R*, 5S*)-3-acetamido-4,5-(cyclohexylidenedioxy)hexanoate (73 mg, 0.214 mmole) was dissolved in 20 ml of isopropyl alcohol, and concentrated hydrochloric acid was added to about 0.01N. The solution was heated under reflux for 45 minutes, and the solvent was removed under reduced pressure. The residue was subjected to TLC, and (4R*, 5S*)-3-acetamido-5-hydroxy-4-hexanolide (20 mg, yield 50%) was isolated.

Rf: 0.22 (ethyl acetate).

$^1$H NMR (acetin, d$_6$): δ 1.32 (d, 3H), 2.08 (s, 3H), 2.50 (dd, J=17, 1.5 Hz, 1H), 2.98 (dd, J=17, 7 Hz, 1H), 3.5–3.9 (m, 2H), 4.15 (dd, J=7.5, 4.0 Hz, 1H), 4.5–4.8 (m, 1H), 7.8 (br, 1H).

From these $^1$H NMR data ($J_{3,4}=7.5$ Hz), the above product was found to have the same configuration as acosamine. Furthermore, since an isomer corresponding to ristosamine was not detected by the $^1$H NMR analysis, it may be safely said that the above product has a purity of more than 95%.

The lactone obtained by the above method can be converted to acosamine methyl ether or acosamine by reducing it with diisobutylaluminum hydride and treating the product with methanol or water under acidic conditions by the method described in the literature reference [J. C. S. Chem. Comm., 442 (1980)].

What is claimed is:

1. A compound represented by the general formula

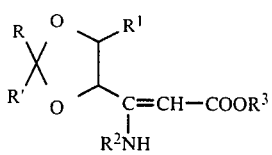 (I)

wherein each of R and R' represents a hydrogen atom, or an alkyl or aryl group or R and R', taken together, form an alkylene group, R$^1$ represents a lower alkyl group, R$^2$ represents a hydrogen atom or an acyl group, and R$^3$ represents a lower alkyl group.

2. The compound of claim 1 wherein each of R and R' represents a lower alkyl group or a phenyl group, or R and R', taken together, represents an alkylene group having 5 to 12 carbon atoms.

3. The compound of claim 1 wherein R$^1$ is a methyl group.

4. The compound of claim 1 wherein R$^2$ represents a hydrogen atom, a lower alkanoyl group or a lower haloalkanoyl group.

5. The compound of claim 1 which is t-butyl (4R, 5S)-3-amino-4,5-(cyclohexylidenedioxy)-2-hexenoate.

6. The compound of claim 1 which is t-butyl (4S, 5S)-3-amino-4,5-(cyclohexylidenedioxy)-2-hexenoate.

7. The compound of claim 1 which is ethyl (4S, 5S)-3-amino-4,5-(cyclohexylidenedioxy)-2-hexenoate.

8. A process for producing the compound of claim 1, which comprises reacting a compound of the formula

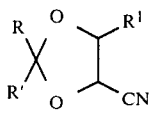 (II)

wherein R, R' and R$^1$ are as defined in claim 1, with an acetic acid ester of the formula

CH$_3$COOR$^3$ (III)

wherein R$^3$ is as defined in claim 1, and as required, acylating the resulting compound of the formula

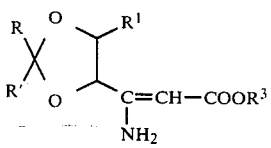 (Ia)

wherein R, R', R$^1$ and R$^3$ are as defined above.

* * * * *